(12) United States Patent
Sjoeholm et al.

(10) Patent No.: US 9,458,445 B2
(45) Date of Patent: Oct. 4, 2016

(54) POLYPEPTIDES HAVING PROTEASE ACTIVITY

(71) Applicant: Novozymes A/S, Bagsvaerd (DK)

(72) Inventors: Carsten Sjoeholm, Virum (DK); Peter Rahbek Oestergaard, Virum (DK); Tine Hoff, Holte (DK); Robert Piotr Olinski, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/877,256

(22) Filed: Oct. 7, 2015

(65) Prior Publication Data

US 2016/0046920 A1    Feb. 18, 2016

Related U.S. Application Data

(62) Division of application No. 14/237,189, filed as application No. PCT/EP2012/066099 on Aug. 17, 2012, now abandoned.

(60) Provisional application No. 61/525,906, filed on Aug. 22, 2011.

(30) Foreign Application Priority Data

Aug. 19, 2011 (EP) .................................. 11178201

(51) Int. Cl.
| | |
|---|---|
| *C12N 9/50* | (2006.01) |
| *C12N 9/52* | (2006.01) |
| *C11D 3/38* | (2006.01) |
| *C12N 15/82* | (2006.01) |
| *C11D 3/386* | (2006.01) |

(52) U.S. Cl.
CPC ............... *C12N 9/50* (2013.01); *A23K 20/189* (2016.05); *C11D 3/386* (2013.01); *C12N 9/52* (2013.01); *C12N 15/8257* (2013.01); *C12Y 304/21* (2013.01); *C12Y 304/2108* (2013.01)

(58) Field of Classification Search
None
See application file for complete search history.

(56) References Cited

U.S. PATENT DOCUMENTS

2006/0259995 A1    11/2006    Cayouette et al.

FOREIGN PATENT DOCUMENTS

| WO | 95/28850 A1 | 11/1995 |
|---|---|---|
| WO | 01/58275 A2 | 8/2001 |
| WO | 01/58276 A2 | 8/2001 |
| WO | 2004/034776 A2 | 4/2004 |
| WO | 2004/072221 A2 | 8/2004 |
| WO | 2004/072279 A2 | 8/2004 |
| WO | 2004/077960 A1 | 9/2004 |
| WO | 2004/111220 A1 | 12/2004 |
| WO | 2004/111223 A1 | 12/2004 |
| WO | 2005/035747 A1 | 4/2005 |
| WO | 2005/123911 A2 | 12/2005 |

OTHER PUBLICATIONS

Cayouette et al., Geneseq Accession No. ADM 99133 (2004).
Henderson et al., Journal of Bacteriology, vol. 169, No. 8, pp. 3778-3784 (1987).
Lucas et al., UniProt Accession No. C1WJ16 (2009).

*Primary Examiner* — Suzanne M Noakes
(74) *Attorney, Agent, or Firm* — Elias Lambiris

(57) ABSTRACT

The present invention relates to isolated polypeptides having protease activity and isolated polynucleotides encoding the polypeptides. The invention also relates to nucleic acid constructs, vectors, and host cells comprising the polynucleotides as well as methods of producing and using the polypeptides in e.g. animal feed and detergents.

20 Claims, No Drawings

US 9,458,445 B2

POLYPEPTIDES HAVING PROTEASE ACTIVITY

CROSS-REFERENCE TO RELATED APPLICATIONS

This application is a divisional of U.S. application Ser. No. 14/237,189 filed on Feb. 5, 2014, now abandoned, which is a 35 U.S.C. 371 national application of PCT/EP2012/066099 filed Aug. 17, 2012, which claims priority or the benefit under 35 U.S.C. 119 of European application No. 11178201.7 filed Aug. 19, 2011 and U.S. provisional application No. 61/525,906 filed Aug. 22, 2011. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular the use of the proteases in animal feed, and detergents.

2. Background of the Invention

In the use of proteases in animal feed (in vivo), and/or the use of such proteases for treating vegetable proteins (in vitro) it is noted that proteins are essential nutritional factors for animals and humans. Most livestock and human beings get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal solids is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many fish the stomach exhibits strongly acidic pH as low as pH 1-2, while the intestine exhibit a more neutral pH in the area pH 6-7. Poultry in addition to stomach and intestine also have a crop preceding the stomach, pH in the crop is mostly determined by the feed ingested and hence typically lies in the range pH 4-6. Protein digestion by a protease may occur along the entire digestive tract, given that the protease is active and survives the conditions in the digestive tract. Hence, proteases which are highly acid stable for survival in the gastric environment and at the same time are efficiently active at broad physiological pH of the target animal are especially desirable.

Also, animal feed is often formulated in pelleted form, where steam is applied in the pelleting process. It is therefore also desireable that proteases used in animal feed are capable to remain active after exposure to steam treatment Polypeptides Having Protease Activity Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 223: 1-5 (1994); Eur. J. Biochem. 232: 1-6 (1995); Eur. J. Biochem. 237: 1-5 (1996); Eur. J. Biochem. 250: 1-6 (1997); and Eur. J. Biochem. 264: 610-650 (1999); respectively. The nomenclature is regularly supplemented and updated; see, e.g., www.chem.qmw.ac.uk/iubmb/enzyme/index.html.

The proteases of the invention and for use according to the invention are selected from the group consisting of:

(a) proteases belonging to the EC 3.4.21. enzyme group; and/or (b) Serine proteases of the peptidase family S1, or more specifically S1A; as described in *Biochem. J.* 290: 205-218 (1993) and in MEROPS protease database, release, 9.4 (31 Jan. 2011) (www.merops.ac.uk). The database is described in Rawlings et al., 2010, MEROPS: the peptidase database. *Nucleic Acids Res.* 38: D227-D233.

More specifically the proteases of the invention are those that prefer a hydrophobic aromatic aa residue in the P1 position.

For determining whether a given protease is a Serine protease, and a family S1A protease, reference is made to the above Handbook and the principles indicated therein. Such determination can be carried out for all types of proteases, be it naturally occurring or wild-type proteases; or genetically engineered or synthetic proteases.

The peptidases of family S1 contain the catalytic triad His, Asp and Ser in that order. Mutation of any of the amino acids of the catalytic triad will result in loss of enzyme activity. The amino acids of the catalytic triad of the S1 protease 1 from *Kribbella solani* (SEQ ID NO: 2) and *Kribbella aluminosa* (SEQ ID NO: 4) are probably positions His-138, Asp-168 and Ser-250.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 5, 10, 15, 20, 25, 30, 35, 37, 40, 45, 50, 55, 60, 65, 70, 80, 90, or 95° C. Examples of protease substrates are casein, such as Azurine-Crosslinked Casein (AZCL-casein), or suc-AAPF-pNA. Examples of suitable protease assays are described in the experimental part.

DESCRIPTION OF THE RELATED ART

Proteases isolated from *Kribbella*, and *Streptomyces* are known in the art. A protease from *Kribbella flavida* is disclosed in Lucas, S. et al. "The complete genome of *Kribbella flavida* DSM 17836"; Submitted (September-2009) to the EMBL/GenBank/DDBJ databases (SWISSPROT: C1WJ16; SEQ ID NO: 6). The sequence has 80.23% identity to the sequence of SEQ ID NO: 2 and 80.81% identity to the sequence of SEQ ID NO: 4 for the mature protease. The DNA sequence of the reference (SEQ ID NO: 5) has an identity of 81.6% to the sequence of sequence of SEQ ID NO: 1 and 85.51% identity to the sequence of SEQ ID NO: 3.

A protease, Streptogrisin B, is disclosed in Henderson et al., 1987, "Characterization and structure of genes for proteases A and B from *Streptomyces griseus*", *J. Bacteriol.* 169: 3778-3784. Sequence identities for this protease are lower than those indicated above:

The present invention provides polypeptides having protease activity and polynucleotides encoding the polypeptides. The proteases of the invention are serine proteases of the peptidase family S1A. The proteases of the invention exhibit surprising pH properties, especially pH stability and pH-activity properties which makes them interesting candidates for use in animal feed. The proteases of the invention thus are active on Suc-Ala-Ala-Pro-Phe-pNA within a broad range from pH 4-11 and exhibit especially high activity in the range pH 6-11, are active on a feed relevant soybean meal-maize meal substrate within a broad physiological pH range from pH 3-7 and retains more than 80% activity after being subjected for 2 hours to pH as low as 2.

The use of proteases in animal feed to improve digestion of proteins in the feed is known. WO 95/28850 discloses the combination of a phytase and one or more microbial proteolytic enzymes to improve the solubility of vegetable proteins. WO 01/58275 discloses the use of acid stable proteases of the subtilisin family in animal feed. WO 01/58276 discloses the use in animal feed of acid-stable proteases related to the protease derived from *Nocardiopsis* sp. NRRL 18262 (the 10R protease), as well as a protease derived from *Nocardiopsis alba* DSM 14010. WO 2004/072221, WO 2004/111220, WO 2004/111223, WO 2005/035747, and WO 2005/123911 disclose proteases related to the 10R protease and their use in animal feed. Also, WO 04/072279 discloses the use of other proteases.

WO 2004/034776 discloses the use of a subtilisin/keratinase, PWD-1 from *B. licheniformis* in the feed of poultry. WO 2004/077960 discloses a method of increasing digestibility of forage or grain in ruminants by applying a bacterial or fungal protease.

Commercial products comprising a protease and marketed for use in animal feed include RONOZYME® ProAct (DSM NP/Novozymes), Axtra® (Danisco), Avizyme® (Danisco), Porzyme® (Danisco), Allzyme™ (Alltech), Versazyme® (BioResources, Int.), Poultrygrow™ (Jefo) and Cibenza® DP100 (Novus).

SUMMARY OF THE INVENTION

The present invention relates to isolated polypeptides having protease activity selected from the group consisting of:

(a) a polypeptide having at least 85% sequence identity to the mature polypeptide of either SEQ ID NO: 2 or SEQ ID NO: 4;

(b) a polypeptide encoded by a polynucleotide having at least 86% sequence identity to the mature polypeptide coding sequence of SEQ ID NO: 1 or SEQ ID NO: 3;

(c) a variant comprising a substitution, deletion, and/or insertion of one or more (several) amino acids of the mature polypeptide of SEQ ID NO: 2; or SEQ ID NO: 4; and (d) a fragment of a polypeptide of (a), (b), or (c), that has protease activity.

The present invention also relates to isolated polynucleotides encoding the polypeptides of the present invention, nucleic acid constructs, recombinant expression vectors, and recombinant host cells comprising the polynucleotides, and to methods of producing the polypeptides.

The present invention also relates to methods for preparing a composition for use in animal feed, for improving the nutritional value of an animal feed, and methods of treating proteins to be used in animal feed compositions.

Furthermore the present invention also relates to the use of the proteases in detergent compositions and such detergent compositions.

Overview of Sequence Listing

SEQ ID NO: 1 is the DNA sequence as isolated from the *Kribbella solani*.

SEQ ID NO: 2 is the amino acid sequence as deduced from SEQ ID NO: 1

SEQ ID NO: 3 is the DNA sequence as isolated from the *Kribbella aluminosa*

SEQ ID NO: 4 is the amino acid sequence as deduced from SEQ ID NO: 3

SEQ ID NO: 5 is the DNA sequence from *Kribbella flavida* (EMBL:CP001736)

SEQ ID NO: 6 is the amino acid sequence from *Kribbella flavida* (Lucas et al., "The complete genome of *Kribbella flavida* DSM 17836." UNIPROT:D2Q1F6)

SEQ ID NO: 7 is the DNA sequence of the 10R protease (WO 05/035747, SEQ ID NO: 1)

SEQ ID NO:8 is the amino acid sequence of the 10R protease (WO 2005/035747, SEQ ID NO: 2)

SEQ ID NO: 9 is the *Kribbella solani* S1 peptidase specific primer forward.

SEQ ID NO: 10 is the *Kribbella solani* S1 peptidase specific primer reverse.

SEQ ID NO: 11 is the *Kribbella aluminosa* S1 peptidase specific primer forward.

SEQ ID NO: 12 is the *Kribbella aluminosa* S1 peptidase specific primer reverse.

SEQ ID NO: 13 Upstream flanking fragment specific primer forward.

SEQ ID NO: 14 Upstream flanking fragment specific primer reverse.

SEQ ID NO: 15 Downstream flanking fragment specific primer forward.

SEQ ID NO: 16 Downstream flanking fragment specific primer reverse.

SEQ ID NO: 17 is a *Bacillus lentus* secretion signal.

Identity Matrix of Sequences

| Protein | SEQ ID NO: 2 | SEQ ID NO: 4 | SEQ ID NO: 6 *Kribbella flavida* | SEQ ID NO: 8 10R protease |
|---|---|---|---|---|
| SEQ ID NO: 2 | 100 | 95 | 80.23 | 46.41 |
| SEQ ID NO: 4 | | 100 | 80.81 | 47.51 |
| SEQ ID NO: 6 | | | 100 | 60.23 |
| SEQ ID NO: 8 | | | | 100 |

| DNA | SEQ ID NO: 1 | SEQ ID NO: 3 | SEQ ID NO: 5 *Kribbella flavida* | SEQ ID NO: 7 10R protease |
|---|---|---|---|---|
| SEQ ID NO: 1 | 100 | 90.76 | 81.82 | 70.96 |
| SEQ ID NO: 3 | 90.76 | 100 | 85.51 | 72.92 |

| | | |
|---|---|---|
| SEQ ID NO: 5 | 100 | 72.68 |
| SEQ ID NO: 7 | | 100 |

Definitions

Protease activity: The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below.

The polypeptides of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 2 or SEQ ID NO: 4.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

An "isolated polypeptide" is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 188 in the numbering of SEQ ID NO: 2, amino acids −105 to −75 in the numbering of SEQ ID NO: 2 is a signal peptide. In a further aspect, the mature polypeptide is amino acids 1 to 189 in the numbering of SEQ ID NO: 4, amino acids −105 to −75 in the numbering of SEQ ID NO: 4 is a signal peptide.

Mature polypeptide coding sequence: The term "mature polypeptide coding sequence" means a polynucleotide that encodes a mature polypeptide having protease activity. In one aspect, the mature polypeptide coding sequence is nucleotides 316 to 879 in the numbering of SEQ ID NO: 1. Further nucleotides 1 to 90 in the numbering of SEQ ID NO: 1 encode a signal peptide. In a further aspect, the mature polypeptide coding sequence is nucleotides 316 to 882 in the numbering of SEQ ID NO: 1. Further nucleotides 1 to 90 in the numbering of SEQ ID NO: 1 encode a signal peptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment− Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has protease activity. In one aspect, a fragment contains at least 168 amino acid residues (e.g., amino acids 11 to 178 of SEQ ID NO: 2), at least 178 amino acid residues (e.g., amino acids 6 to 183 of SEQ ID NO: 2); or correspondingly for SEQ ID NO: 4 a fragment contains at least 169 amino acid residues (e.g., amino acids 11 to 179 of SEQ ID NO: 4) or at least 180 amino acid residues (e.g., amino acids 5 to 184 of SEQ ID NO: 4).

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 504 nucleotides (e.g., nucleotides 346 to 849 of SEQ ID NO: 1), or e.g., at least 534 nucleotides (e.g., nucleotides 331 to 864 of SEQ ID NO: 1); or correspondingly for SEQ ID NO: 3 a fragment contains at least 507 nucleotides (e.g. nucleotides 346 to 852 of SEQ ID NO: 3) or e.g. at least 540 nucleotides (e.g. nucleotides 328 to 867 of SEQ ID NO: 3).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Polypeptides Having Protease Activity

The present invention relates to isolated polypeptides having protease activity selected from the group consisting of:

(a) a polypeptide having at least 85% sequence identity to the mature polypeptide of SEQ ID NO: 2 and SEQ ID NO: 4;

(b) a polypeptide encoded by a polynucleotide that hybridizes under high stringency conditions, or very high stringency conditions with
   (i) the mature polypeptide coding sequence of SEQ ID NO: 1, and/or
   (ii) the mature polypeptide coding sequence of SEQ ID NO: 3, or
   (iii) the full-length complementary strand of (i) or (ii);

(c) a polypeptide encoded by a polynucleotide having at least 86% sequence identity to the mature polypeptide coding sequence of SEQ ID NO: 1 or SEQ ID NO: 3; and/or (d) a variant comprising a substitution, deletion, and/or insertion of one or more (several) amino acids of the mature polypeptide of SEQ ID NO: 2; and SEQ ID NO: 4.

The present invention relates to isolated polypeptides having a sequence identity to the mature polypeptide of SEQ ID NO: 2 of at least 85%, e.g., at least 87%, at least 89%, at least 90%, at least 93%, at least 95%, at least 96%, at least 97%, at least 98%, at least 99%, or 100%, which have protease activity. In one aspect, the polypeptides differ by no more than ten amino acids, e.g., by nine amino acids, by eight amino acids, by seven amino acids, by six amino acids, by five amino acids, by four amino acids, by three amino acids, by two amino acids, and by one amino acid from the mature polypeptide of SEQ ID NO: 2.

An embodiment of the invention is a polypeptide or a polypeptide encoded by a polynucleotide having at least 87% sequence identity to the polypeptide of SEQ ID NO: 2.

An embodiment of the invention is a polypeptide or a polypeptide encoded by a polynucleotide having at least 89% sequence identity to the polypeptide of SEQ ID NO: 2.

An embodiment of the invention is a polypeptide or a polypeptide encoded by a polynucleotide having at least 90% sequence identity to the polypeptide of SEQ ID NO: 2.

An embodiment of the invention is a polypeptide or a polypeptide encoded by a polynucleotide having at least 93% sequence identity to the polypeptide of SEQ ID NO: 2.

An embodiment of the invention is a polypeptide or a polypeptide encoded by a polynucleotide having at least 95% sequence identity to the polypeptide of SEQ ID NO: 2.

An embodiment of the invention is a polypeptide or a polypeptide encoded by a polynucleotide having at least 96% sequence identity to the polypeptide of SEQ ID NO: 2.

An embodiment of the invention is a polypeptide or a polypeptide encoded by a polynucleotide having at least 97% sequence identity to the polypeptide of SEQ ID NO: 2.

An embodiment of the invention is a polypeptide or a polypeptide encoded by a polynucleotide having at least 98% sequence identity to the polypeptide of SEQ ID NO: 2.

An embodiment of the invention is a polypeptide or a polypeptide encoded by a polynucleotide having at least 99% sequence identity to the polypeptide of SEQ ID NO: 2.

An embodiment of the invention is a polypeptide or a polypeptide encoded by a polynucleotide having at least 100% sequence identity to the polypeptide of SEQ ID NO: 2.

The present invention relates to isolated polypeptides having a sequence identity to the mature polypeptide of SEQ ID NO: 4 of at least 85%, e.g., at least 87%, at least 89%, at least 90%, at least 93%, at least 95%, at least 96%, at least 97%, at least 98%, at least 99%, or 100%, which have protease activity. In one aspect, the polypeptides differ by no more than twentyfive amino acids, e.g., by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 4.

An embodiment of the invention is a polypeptide or a polypeptide encoded by a polynucleotide having at least 87% sequence identity to the polypeptide of SEQ ID NO: 4.

An embodiment of the invention is a polypeptide or a polypeptide encoded by a polynucleotide having at least 89% sequence identity to the polypeptide of SEQ ID NO: 4.

An embodiment of the invention is a polypeptide or a polypeptide encoded by a polynucleotide having at least 90% sequence identity to the polypeptide of SEQ ID NO: 4.

An embodiment of the invention is a polypeptide or a polypeptide encoded by a polynucleotide having at least 93% sequence identity to the polypeptide of SEQ ID NO: 4.

An embodiment of the invention is a polypeptide or a polypeptide encoded by a polynucleotide having at least 95% sequence identity to the polypeptide of SEQ ID NO: 4.

An embodiment of the invention is a polypeptide or a polypeptide encoded by a polynucleotide having at least 96% sequence identity to the polypeptide of SEQ ID NO: 4.

An embodiment of the invention is a polypeptide or a polypeptide encoded by a polynucleotide having at least 97% sequence identity to the polypeptide of SEQ ID NO: 4.

An embodiment of the invention is a polypeptide or a polypeptide encoded by a polynucleotide having at least 98% sequence identity to the polypeptide of SEQ ID NO: 4.

An embodiment of the invention is a polypeptide or a polypeptide encoded by a polynucleotide having at least 99% sequence identity to the polypeptide of SEQ ID NO: 4.

An embodiment of the invention is a polypeptide or a polypeptide encoded by a polynucleotide having at least 100% sequence identity to the polypeptide of SEQ ID NO: 4.

A polypeptide of the present invention preferably comprises or consists of the amino acid sequence of SEQ ID NO: 2 or SEQ ID NO: 4 or an allelic variant thereof; or is a fragment thereof having protease activity. In another aspect, the polypeptide comprises or consists of the mature polypeptide of SEQ ID NO: 2 or SEQ ID NO: 4. In another preferred aspect, the polypeptide comprises or consists of amino acids 1 to 188 of SEQ ID NO: 2, or amino acids 1 to 189 of SEQ ID NO: 4.

The present invention also relates to isolated polypeptides having protease activity that are encoded by polynucleotides that hybridize under high stringency conditions, or very high stringency conditions with (i) the mature polypeptide coding sequence of SEQ ID NO: 1 or SEQ ID NO: 3, (ii) [the genomic DNA sequence comprising] the mature polypeptide coding sequence of SEQ ID NO: 1 or SEQ ID NO: 3, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1 or SEQ ID NO: 3; or a subsequence thereof, as well as the amino acid sequence of SEQ ID NO: 2 or SEQ ID NO: 4, or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3; or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1 or SEQ ID NO: 3; [the genomic DNA sequence comprising] the mature polypeptide coding sequence of SEQ ID NO: 1 or SEQ ID NO: 3; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1 or SEQ ID NO: 3. In another aspect, the nucleic acid probe is a fragment thereof. In another aspect, the nucleic acid probe is a polynucleotide that encodes the polypeptide of SEQ ID NO: 2 or SEQ ID NO: 4 or a fragment thereof. In another preferred aspect, the nucleic acid probe is SEQ ID NO: 1 or SEQ ID NO: 3.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having protease activity encoded by polynucleotides having a sequence identity to the mature polypeptide coding sequence of SEQ ID NO: 1 of at least 86%, at least 90%, at least 95%, at least 96%, at least 97%, at least 98%, at least 99%, or 100%.

An embodiment of the invention is polypeptides having protease activity encoded by polynucleotides having a sequence identity to the mature polypeptide coding sequence of SEQ ID NO: 1 of at least 86%.

An embodiment of the invention is polypeptides having protease activity encoded by polynucleotides having a sequence identity to the mature polypeptide coding sequence of SEQ ID NO: 1 of at least 90%.

An embodiment of the invention is polypeptides having protease activity encoded by polynucleotides having a sequence identity to the mature polypeptide coding sequence of SEQ ID NO: 1 of at least 95%.

An embodiment of the invention is polypeptides having protease activity encoded by polynucleotides having a sequence identity to the mature polypeptide coding sequence of SEQ ID NO: 1 of at least 96%.

An embodiment of the invention is polypeptides having protease activity encoded by polynucleotides having a sequence identity to the mature polypeptide coding sequence of SEQ ID NO: 1 of at least 97%.

An embodiment of the invention is polypeptides having protease activity encoded by polynucleotides having a sequence identity to the mature polypeptide coding sequence of SEQ ID NO: 1 of at least 98%.

An embodiment of the invention is polypeptides having protease activity encoded by polynucleotides having a sequence identity to the mature polypeptide coding sequence of SEQ ID NO: 1 of at least 99%.

An embodiment of the invention is polypeptides having protease activity encoded by polynucleotides having a sequence identity to the mature polypeptide coding sequence of SEQ ID NO: 1 of at least 100%.

The present invention also relates to isolated polypeptides having protease activity encoded by polynucleotides having a sequence identity to the mature polypeptide coding sequence of SEQ ID NO: 3 of at least 86%, at least 90%, at least 95%, at least 96%, at least 97%, at least 98%, at least 99%, or 100%.

An embodiment of the invention is polypeptides having protease activity encoded by polynucleotides having a sequence identity to the mature polypeptide coding sequence of SEQ ID NO: 3 of at least 86%.

An embodiment of the invention is polypeptides having protease activity encoded by polynucleotides having a sequence identity to the mature polypeptide coding sequence of SEQ ID NO: 3 of at least 90%.

An embodiment of the invention is polypeptides having protease activity encoded by polynucleotides having a sequence identity to the mature polypeptide coding sequence of SEQ ID NO: 3 of at least 95%.

An embodiment of the invention is polypeptides having protease activity encoded by polynucleotides having a sequence identity to the mature polypeptide coding sequence of SEQ ID NO: 3 of at least 96%.

An embodiment of the invention is polypeptides having protease activity encoded by polynucleotides having a sequence identity to the mature polypeptide coding sequence of SEQ ID NO: 3 of at least 97%.

An embodiment of the invention is polypeptides having protease activity encoded by polynucleotides having a sequence identity to the mature polypeptide coding sequence of SEQ ID NO: 3 of at least 98%.

An embodiment of the invention is polypeptides having protease activity encoded by polynucleotides having a sequence identity to the mature polypeptide coding sequence of SEQ ID NO: 3 of at least 99%.

An embodiment of the invention is polypeptides having protease activity encoded by polynucleotides having a sequence identity to the mature polypeptide coding sequence of SEQ ID NO: 3 of at least 100%.

In particular embodiments, the parent proteases and/or the protease variants of the invention and for use according to the invention are selected from the group consisting of:

(a) Proteases belonging to the EC 3.4.21 enzyme group; and
(b) Serine proteases of peptidase family S1A; as described in Biochem.J. 290:205-218 (1993) and in MEROPS protease database, release 9.5 (www.merops.ac.uk). The database is described in Rawlings et al., 2010, MEROPS: the peptidase database, *Nucleic Acids Res.* 38: D227-D233.

For determining whether a given protease is a Serine protease, and a family S1A protease, reference is made to the above Handbook and the principles indicated therein. Such determination can be carried out for all types of proteases, be it naturally occurring or wild-type proteases; or genetically engineered or synthetic proteases.

The present invention also relates to variants comprising a substitution, deletion, and/or insertion of one or more (or several) amino acids of the mature polypeptide of SEQ ID NO: 2 or SEQ ID NO: 4, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 or SEQ ID NO: 4 is not more than 20, e.g., 1, 2, 3, 4, 5, 6, 7, 8, 9, 10, 11, 12, 13, 14, 15, 16, 17, 18, 19 or 20.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987;

Carter et al., 1989, *Proteins: Structure, Function, and Genetics* 6: 240-248; and Stevens, 2003, *Drug Discovery World* 4: 35-48.

The proteases of the invention exhibit surprising pH properties, especially pH stability and pH-activity properties, especially at low pH values, which makes them interesting candidates for use in animal feed and detergents.

Embodiments

In certain embodiments of the invention, the protease of the invention exhibits beneficial thermal properties such as thermostability, steam stability, etc and/or pH properties, such as acid stability, pH optimum, etc.

An embodiment of the invention is isolated polypeptides having improved protease activity between pH 4 and 9, such as between pH 5 and 8, such as at pH 5, at pH 6, at pH 7 or at pH 8, at 25° C. compared to protease 10R.

An additional embodiment of the invention is improved protease activity on soybean-maize meal between pH 3.0 and 6.0 at 40° C., such as at pH 3.0, at pH 4.0, at pH 5.0 or at pH 6.0, compared to protease 10R.

Acidity/Alkalinity Properties

In certain embodiments of the invention the protease of the invention exhibits beneficial properties in respect of pH, such as acid stability, pH optimum, etc. Stability of the protease at a low pH is beneficial since the protease can have activity in the intestine after passing through the stomach. In one embodiment of the invention the protease retains >95% activity after 2 hours at pH 3 as determined using the method described in Example 3.

Thermostability

Thermostability may be determined as described in Example 6, i.e. using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 5, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 5.

In still further particular embodiments, the thermostable protease of the invention has a melting temperature, $T_m$ (or a denaturation temperature, $T_d$), as determined using Differential Scanning calorimetry (DSC) as described in example 10 (i.e. in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 7 by determining the residual activity of protease molecules after steam treatment at 85° C. or 90° C. for a short time.

Pelleting Stability

Pelleting stability may be determined as described in Example 8 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such as *Actinobacteria* or from a gram-negative bacterium within a phylum such as *Proteobacteria*.

In one aspect, the polypeptide is a protease from a bacterium of the class *Actinobacteria*, such as from the order *Actinomycetales*, or from the suborder Propionibacterineae, or from the family Nocardioidaceae, or from the genera *Kribbella, Saccharomonospora, Saccharopolyspora*; or *Amycolatopsis*.

Strains of these taxa are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Kribbella*, or another or related organism from the *Actinomycetales* and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 or SEQ ID NO: 3 of at least 86%, at least 90%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or SEQ ID NO: 3, (ii the genomic DNA sequence comprising the mature polypeptide coding sequence of SEQ ID NO: 1 or SEQ ID NO: 3, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1 or SEQ ID NO: 3, the mature polypeptide coding sequence of SEQ ID NO: 1, or a subsequence of SEQ ID NO: 1 or SEQ ID NO: 3 that encodes a fragment of SEQ ID NO: 2 or SEQ ID NO: 4 having protease activity, such as the polynucleotide of nucleotides 316 to 879 of SEQ ID NO: 1 or nucleotides 316 to 882 SEQ ID NO: 3.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but are not limited to, *Bacillus, Brevibacillus, Clostridium, Geobacillus, Lactobacillus, Lactococcus, Paenibacillus,* and *Streptomyces*. Gram-negative bacteria include, but are not limited to *E. coli*, and *Pseudomonas*.

The bacterial host cell may be any *Bacillales* cell including, but not limited to, *Bacillus amyloliquefaciens, Brevibacillus brevis, Bacillus circulans, Bacillus clausii, Bacillus coagulans, Bacillus lentus, Bacillus licheniformis, Geobacillus stearothermophilus, Bacillus subtilis,* and *Bacillus thuringiensis* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Kribbella*. In a more preferred aspect, the cell is *Kribbella solani* or *Kribbella aluminosa*.

The present invention also relates to methods of producing a polypeptide of the present invention, comprising: (a)

cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1.

The composition may comprise a protease of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by microorganisms such as bacteria or fungi or by plants or by animals. The compositions may be prepared in accordance with methods known in the art and may be in the form of a liquid or a dry composition. For instance, the composition may be in the form of a granulate or a microgranulate. The protease may be stabilized in accordance with methods known in the art.

Uses

The present invention is also directed to methods for using the polypeptides having protease activity, or compositions thereof.

Animal Feed

The present invention is also directed to methods for using the proteases having protease activity in animal feed, as well as to feed compositions and feed additives comprising the proteases of the invention.

The term animal includes all animals, including human beings. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or *quinoa*.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, eg an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g., by a heat-treatment step.

In another particular embodiment of a treatment process of the invention, the protease action is sustained, meaning, e.g., that the protease is added to the proteins, but its hydrolysing influence is so to speak not switched on until later when desired, once suitable hydrolysing conditions are established, or once any enzyme inhibitors are inactivated, or whatever other means could have been applied to postpone the action of the enzyme.

In one embodiment the treatment is a pre-treatment of animal feed or proteins for use in animal feed, i.e., the proteins are hydrolyzed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e. the weight of ingested feed relative to weight gain) of the animal might be improved.

The protease can be added to the feed in any form, be it as a relatively pure protease, or in admixture with other components intended for addition to animal feed, i.e. in the form of animal feed additives, such as the so-called premixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g. carotenoids such as beta-carotene, astaxanthin, and lutein; stabilisers; growth improving additives and aroma compounds/flavorings, e.g. creosol, anethol, deca-, undeca- and/or dodeca-lactones, ionones, irone, gingerol, piperidine, propylidene phatalide, butylidene phatalide, capsaicin and/or tannin; antimicrobial peptides; polyunsaturated fatty acids (PUFAs); reactive oxygen generating species; also, a support may be used that may contain, for example, 40-50% by weight of wood fibres, 8-10% by weight of stearine, 4-5% by weight of *curcuma* powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthethase.

Usally fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (')/0 meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically a liquid protease/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet. The protease should of course be applied in an effective amount, i.e. in an amount adequate for improving hydrolysis, digestibility, and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Detergent Compositions

The protease of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258068 and EP 305216 or from *H. insolens* as described in WO 96/13580, a *Pseudomonas* lipase, e.g. from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S). Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes NS), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544. Commercially available cellulases include Celluzyme™, and Carezyme™ (Novozymes NS), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

When included therein the detergent may contain a hydrotrope, which is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, or a peptide aldehyde as described in, e.g., WO 2010/055052, and the composition may be formulated as described in e.g. WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Nucleic Acid Constructs, Expression Vectors, Recombinant Host Cells, and Methods for Production of Proteases The present invention also relates to nucleic acid constructs, expression vectors and recombinant host cells comprising such polynucleotides encoding the proteases of the invention.

The present invention also relates to methods of producing a protease, comprising: (a) cultivating a recombinant host cell comprising such polynucleotide; and (b) recovering the proten.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials and Methods
Assays:
Protease Assays:
1) Suc-AAPF-pNA assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

2) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM $CaCl_2$, 150 mM KCl, 0.01% Triton X-100, pH 6.5 or pH 7.0.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).

3) Suc-AAPX-pNA Assay:
pNA substrates: Suc-AAPA-pNA (Bachem L-1775)
  Suc-AAPR-pNA (Bachem L-1720)
  Suc-AAPD-pNA (Bachem L-1835)
  Suc-AAPI-pNA (Bachem L-1790)
  Suc-AAPM-pNA (Bachem L-1395)
  Suc-AAPV-pNA (Bachem L-1770)
  Suc-AAPL-pNA (Bachem L-1390)
  Suc-AAPE-pNA (Bachem L-1710)
  Suc-AAPK-pNA (Bachem L-1725)
  Suc-AAPF-pNA (Bachem L-1400)
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 9.0.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

Soybean-Maize Meal Assay (SMM Assay)

An end-point assay using soybean-maize meal as substrate was used for obtaining the activity profile of the proteases at pH 3-7.

Assay buffers: 100 mM succinic acid, 100 mM HEPES, 100 mM CHES, 100 mM CAPS, 1 mM $CaCl_2$, 150 mM KCl, 0.01% Triton X-100 adjusted using HCl or NaOH to pH-values 3.0, 4.0, 5.0, 6.0, 7.0, 8.0, 9.0, 10.0 and 11.0 when mixing 10 ml assay buffer with 1 g soybean-maize meal (30:70 ratio).

2 mL soybean-maize meal slurry is mixed for 30 min before protease addition and incubation for 3 hours at 40° C. (500 rpm). Protease is added via 100 µl 100 mM sodium acetate (NaAc) buffer (9.565 g/l NaAc, 1.75 g/l acetic acid, 5 mM $CaCl_2$, 0.01% BSA, 0.01% Tween20, pH 6.0). Supernatant are collected after centrifugation (10 min, 4000 rpm, 0° C.) and protein activity is determined using a colorimetric assay based on the o-phthat-dialdehyde (OPA) method essentially according to Nielsen et al. (Nielsen, P M, Petersen, D, Dampmann, C. Improved method for determining food protein degree of hydrolysis. J Food Sci, 2001, 66: 642-646). This assay detects free α-amino groups and hence protease activity can be measured as an increase in absorbance. First 500 μl of each supernatant is filtered through a 100 kDa Microcon filter by centrifugation (60 min, 11,000 rpm, 5° C.). The samples are diluted 10× in deionized water and 25 μl of each sample is loaded into a 96 well microtiter plate (5 replicates). Finally 200 μl OPA reagent is dispensed into all wells and the plate is shaken (10 sec, 750 rpm) and absorbance measured at 340 nm. The level of protease activity is calculated as the difference between absorbance in the enzyme treated sample and the blank sample.

Results are provided in Example 4 below

In vitro Digestion Assay

An in vitro digestion assay was used to evaluate the effect of the proteases on a feed substrate (soybean-maize meal) in a setup designed to simulate digestion in monogastric animals.

The incubation process consisted of a gastric digestion phase with porcine pepsin (SP7000, Sigma-Aldrich, St. Louis, Mo., USA) at pH 3 followed by a short duodenal incubation at pH 3.8 and a small intestinal incubation with pancreatin (8×USB, P-7545, Sigma-Aldrich, St. Louis, Mo., USA) at pH 7.0.

The in vitro digestion was performed using an automated system based on a Gilson liquid handler (Biolab, Denmark). For each sample 0.8 g feed was weighed into a tube and all tubes were placed in the liquid handler (40° C., 500 rpm). Additions of solutions as well as pH measurements were performed automatically. At time 0 min, 4.1 mL HCl (24 mM $CaCl_2$) was added to reach pH 3.0 in the solution. At time 30 min 0.5 ml HCl (24 mM $CaCl_2$, 3000 U pepsin/g feed) and 100 μL of a 100 mM sodium acetate buffer (258.6 g NaAc per litre, 0.57% acetic acid, pH 6.0) was added. At time 90 min 900 μL NaOH was added to reach pH ~3.8 and at time 120 min 400 μL of a 1 M $NaHCO_3$ solution containing 6.5 mg pancreatin/g feed was added leading to pH 6.8 in the solution. The pH was measured at time 30, 60, 90, 115, 120 and 180 min. The test proteases were added via the 100 μl NaAc buffer at time 30 min.

The level of soluble crude protein (N×6.25) measured using a LECO FP-528 protein/nitrogen analyzer, was used as an indication of protease efficacy in the assay. Statistics: Statistical analysis of the parameters registered was performed using an analysis of variance (ANOVA) procedure and comparison of means was done using the Tukey test ($\alpha=0.05$) provided by the ANOVA procedure (SAS, JMP® 5 Administrators Guide to Annually Licensed Windows, Mackintosh, and Linux Versions, Release 5.1. SAS Institute, Cary, N.C. (2003)).

Results are provided in Example 5 below.

Strains

*Kribbella solani*, isolate 067P2, was isolated from a soil sample from the United Kingdom obtained from Warwick University in 1990.

*Kribbella aluminosa*, isolate 05C3Y, was isolated from a sample from China provided to Novozymes in 2009 under contract with Yunnan Institute of Microbiology; Kunming.

Example 1

DNA-Preparation and Sequencing of the *Kribbella solani* and the *Kribbella aluminosa* Genome Chromosomal DNA of *Kribbella solani* and *Kribbella aluminosa* was isolated by QIAamp DNA Blood Mini Kit" (Qiagen, Hilden, Germany). 5 ug of chromosomal DNA of each strain were sent for genome sequencing at FASTERIS SA, Switzerland. The genomes were sequenced by Illumina Sequencing. The genome sequences were analysed for secreted S1 proteases and the two S1 proteases (SEQ ID:1/SEQ ID:2 and SEQ ID: 3/SeqID:4) where identified.

Expression of *Kribbella solani* and *Kribbella aluminosa* S1 Peptidases

A linear integration vector-system was used for the expression cloning of two 51 peptidase genes from *Kribbella solani* (SEQ ID NO: 1) and *Kribbella aluminosa* (SEQ ID NO: 3), respectively. The linear integration construct was a PCR fusion product made by fusion of the gene between two *Bacillus subtilis* homologous chromosomal regions along with a strong promoter and a chloramphenicol resistance marker. The fusion was made by SOE PCR (Horton et al., 1989, Engineering hybrid genes without the use of restriction enzymes, gene splicing by overlap extension, Gene 77: 61-68). The SOE PCR method is also described in patent application WO 2003/095658. The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* crIIIA promoter including stabilizing sequence. The gene coding for chloramphenicol acetyl-transferase was used as marker (described in, e.g., Diderichsen et al., 1993, A useful cloning vector for *Bacillus subtilis, Plasmid* 30: 312). The final gene constructs were integrated on the *Bacillus* chromosome by homologous recombination into the pectate lyase locus.

The gene fragments of the two genes were amplified from chromosomal DNA of the two strains with specific primers (KS-forward (SEQ ID NO: 9) and KS-reverse (SEQ ID NO: 10) for the S1 protease from *Kribbella solani* and KA-forward (SEQ ID NO: 11) and KA-reverse (SEQ ID NO: 12) for the S1 protease from *Kribbella aluminosa*. The upstream flanking fragment was amplified with the primers 260558 (SEQ ID NO: 13) and iMB1361Uni2 (SEQ ID NO: 14) and the downstream flanking fragment was amplified with the primers 260559 (SEQ ID NO: 15) and oth435 (SEQ ID NO: 16) from genomic DNA of the strain iMB1361 (described in patent application WO 2003/095658).

Both S1 peptidase were expressed with a *Bacillus lentus* secretion signal (with the following amino acid sequence: MKKPLGKIVASTALLISVAFSSSIASA (SEQ ID NO: 17) replacing the native secretion signals. The signal was placed on the upstream flanking fragment. The forward primers were designed so that the genes were amplified from the signal peptide cleavage site and they had 26 bp overhangs and the reverse primers contained an overhang consisting of 24-27 bp (the overhangs are shown in italic in the table below). These overhangs were each complementary to part of one or the other of the two linear vector fragments and was used when the gene fragments and the vector fragments were assembled (described below). All primers used are listed in Table 2 below.

The gene fragments were amplified using a proofreading polymerase PHUSION™ DNA Polymerase (Finnzymes, Finland) according to the manufacturer's instructions. The two flanking DNA fragments were amplified with "Expand High Fidelity PCR System" (Roche-Applied-Science) according to standard procedures (following the manufacturer's recommendations). The PCR conditions were as follows for *Kribbella aluminosa* S1 gene: 98° C. for 30 sec. followed by 35 cycles of (98° C. for 10 sec, 54° C. for 20 sec, 72° C. for 1.5 min) and ending with one cycle at 72° C.

for 10 min. The PCR conditions were as follows for the *Kribbella solani* S1 gene: 98° C. for 30 sec. followed by 35 cycles of (98° C. for 10 sec, 72° C. for 20 sec, 72° C. for 45 sec.) and ending with one cycle at 72° C. for 10 min. For both expression constructs the 3 PCR fragments were subjected to a subsequent Splicing by Overlap Extension (SOE) PCR reaction to assemble the 3 fragments into one linear vector construct.

This was done by mixing the 3 fragments in equal molar ratios and a new PCR reaction were run under the following conditions: initial 2 min. at 94° C., followed by 10 cycles of (94° C. for 15 sec., 55° C. for 45 sec., 68° C. for 5 min.), 10 cycles of (94° C. for 15 sec., 55° C. for 45 sec., 68° C. for 8 min.), 15 cycles of (94° C. for 15 sec., 55° C. for 45 sec., 68° C. for 8 min. in addition 20 sec. extra pr cycle). After the 1$^{st}$ cycle the two end primers 260558 and 260559 were added (20 pMol of each). Two μl of each of the PCR products were transformed into *Bacillus subtilis*. Transformants were selected on LB plates supplemented with 6 μg of chloramphenicol per ml. Two recombinant *Bacillus subtilis* clones each containing one of the integrated expression constructs were grown in liquid cultures. The enzyme containing supernatants were harvested and the two enzymes purified as described in Example 2.

the same buffer over five column volumes. Fractions from the column were analysed for protease activity (using the Suc-AAPF-pNA assay at pH 9). The protease peak was pooled and solid ammonium sulphate was added to the pool to a final ammonium sulphate concentration of 1.8M $(NH_4)_2SO_4$. The ammonium sulphate adjusted pool was applied to a Phenyl-sepharose FF (high sub) column (from GE Healthcare) equilibrated in 100 mM $H_3BO_3$, 10 mM MES/NaOH, 2 mM $CaCl_2$, 1.8M $(NH_4)_2SO_4$, pH 6.0. After washing the column extensively with the equilibration buffer, the protease was eluted with a linear gradient over eight column volumes between the equilibration buffer and 100 mM $H_3BO_3$, 10 mM MES/NaOH, 2 mM $CaCl_2$, pH 6.0 with 25% (v/v) 2-propanol. Fractions from the column were analysed for protease activity (using the Suc-AAPF-pNA assay at pH 9). The protease peak was pooled and the pool was transferred to 50 mM $H_3BO_3$, 20 mM $CH_3COOH$/NaOH, 1 mM $CaCl_2$, pH 4.5 on a G25 Sephadex column (from GE Healthcare). The G25 sephadex transferred enzyme was applied to a SOURCE S column (from GE Healthcare) equilibrated in 50 mM $H_3BO_3$, 20 mM $CH_3COOH$/NaOH, 1 mM $CaCl_2$, pH 4.5. After washing the column extensively with the equilibration buffer, the protease was eluted with a linear NaCl gradient (0-->0.5 M) in the same buffer over

TABLE 2

Primers used

| Amplification of | SPECIFIC PRIMER FORWARD | SPECIFIC PRIMER REVERSE |
|---|---|---|
| *Kribbella solani* S1 peptidase | KS FORWARD (SEQ ID NO: 9) 5' CTTTTAGTTCATCGATCGCATCGG CT GCACCGGTGAACCCGTCCGCG 3' | KS REVERSE (SEQ ID NO: 10) 5' GGGCCAAGGCCGGTTTTTTATGT TTTAGACGCTGACGCCGTAGCG GGAGAG 3' |
| *Kribbella aluminosa* S1 peptidase | KA forward (SEQ ID NO: 11) 5' CTTTTAGTTCATCGATCGCATCG GCT GCACCGGTCGACCCGTCC 3' | KA reverse (SEQ ID NO: 12) 5' CCAAGGCCGGTTTTTATGTTTC A GTAGACGCTCACGCCGT 3' |
| Upstream flanking fragment | 260558: (SEQ ID NO: 13) 5' GAGTATCGCCAGTAAGGGGCG 3' | iMB1361Uni2 (SEQ ID NO: 14) 5' AGCCGATGCGATCGATGAACTA 3' |
| Downstream flanking fragment | OTH435 (SEQ ID NO: 15) 5' TAAAACATAAAAAACCGGCCTTGG C 3' | 260559: (SEQ ID NO: 16) 5' GCAGCCCTAAAATCGCATAAAGC 3' |

Example 2

Purification of the Proteases

Purification of the S1A Protease from *Kribbella solani*

The culture broth was centrifuged (20000×g, 20 min) and the supernatant was carefully decanted from the precipitate. The supernatant was filtered through a Nalgene 0.2 μm filtration unit in order to remove the rest of the *Bacillus* host cells. The 0.2 μm filtrate was transferred to 50 mM $H_3BO_3$, 20 mM $CH_3COOH$/NaOH, 1 mM $CaCl_2$, pH 4.5 on a G25 Sephadex column (from GE Healthcare). The G25 sephadex transferred enzyme was slightly turbid and was filtered through a GF/A glass microfiber filter (from Whatman). The clear filtrate was applied to a SP-sepharose FF column (from GE Healthcare) equilibrated in 50 mM $H_3BO_3$, 20 mM $CH_3COOH$/NaOH, 1 mM $CaCl_2$, pH 4.5. After washing the column extensively with the equilibration buffer, the protease was eluted with a linear NaCl gradient (0-->0.5 M) in twenty column volumes. Fractions from the column were analysed for protease activity (using the Suc-AAPF-pNA assay at pH 9) and active fractions were further analysed by SDS-PAGE. Fractions, where only one band was seen on the coomassie stained SDS-PAGE gel, were pooled and transferred to 100 mM $H_3BO_3$, 10 mM MES/NaOH, 2 mM CaCl2, pH 6.0 on a G25 Sephadex column (from GE Healthcare). The G25 sephadex transferred enzyme was the purified preparation and was used for further characterization.

Purification of the S1A Protease from *Kribbella aluminosa*

The culture broth was centrifuged (20000×g, 20 min) and the supernatant was carefully decanted from the precipitate. The supernatant was filtered through a Nalgene 0.2 μm filtration unit in order to remove the rest of the *Bacillus* host cells. The 0.2 μm filtrate was transferred to 10 mM succinic acid/NaOH, 1 mM CaCl$_2$, pH 5.0 on a G25 Sephadex column (from GE Healthcare). The G25 sephadex transferred enzyme was slightly turbid and was filtered through a GF/A glass microfiber filter (from Whatman). The clear filtrate was applied to a SP-sepharose FF column (from GE Healthcare) equilibrated in 10 mM succinic acid/NaOH, 1 mM CaCl$_2$, pH 5.0. After washing the column extensively with the equilibration buffer, the protease was eluted with a linear NaCl gradient (0-->0.5 M) in the same buffer over five column volumes. Fractions from the column were analysed for protease activity (using the Suc-AAPF-pNA assay at pH 9). The protease peak was pooled and solid ammonium sulphate was added to the pool to a final ammonium sulphate concentration of 1.2 M (NH$_4$)$_2$SO$_4$. The ammonium sulphate adjusted pool was applied to a Phenyl-Toyopearl column (from TosoHaas) equilibrated in 100 mM H$_3$BO$_3$, 10 mM MES/NaOH, 2 mM CaCl$_2$, 1.2 M (NH$_4$)$_2$SO$_4$, pH 6.0. After washing the column extensively with the equilibration buffer, the protease was eluted with a linear (NH$_4$)$_2$SO$_4$ gradient (1.2-->0 M) in the same buffer over five column volumes. Fractions from the column were analysed for protease activity (using the Suc-AAPF-pNA assay at pH 9) and active fractions were further analysed by SDS-PAGE. Fractions, where only one band was seen on the coomassie stained SDS-PAGE gel, were pooled and the pool was transferred to 10 mM succinic acid/NaOH, 1 mM CaCl$_2$, pH 5.0 on a G25 Sephadex column (from GE Healthcare). The G25 sephadex transferred enzyme was applied to a SOURCE S column (from GE Healthcare) equilibrated in 10 mM succinic acid/NaOH, 1 mM CaCl$_2$, pH 5.0. After washing the column extensively with the equilibration buffer, the protease was step eluted with 10 mM succinic acid/NaOH, 1 mM CaCl$_2$, 0.5 M NaCl, pH 5.0. The eluted peak from the column was the purified preparation and was used for further characterization.

Example 3

Characterization of the S1A Proteases from *Kribbella*

The Suc-AAPF-pNA assay was used for obtaining the pH-activity profile and the pH-stability profile (residual activity after 2 hours at indicated pH-values). For the pH-stability profile the protease was diluted 10× in the different Assay buffers to reach the pH-values of these buffers and then incubated for 2 hours at 37° C. After incubation, the pH of the protease incubations was transferred to the same pH-value, before assay for residual activity, by dilution in the pH 9.0 Assay buffer. The Protazyme AK assay was used for obtaining the temperature-activity profile at pH 6.5 (*Kribbella solani*) or at pH 7.0 (*Kribbella aluminosa*). The Suc-AAPX-pNA assay and ten different Suc-AAPX-pNA substrates were used for obtaining the P1-specificity of the enzymes at pH 9.0.

The results are shown in Tables 3-6 below. For Table 3, the activities are relative to the optimal pH for the enzymes. For Table 4, the activities are residual activities relative to a sample, which was kept at stable conditions (5° C., pH 9.0). For Table 5, the activities are relative to the optimal temperature at pH 6.5 or pH 7.0 for the enzymes. For Table 6, the activities are relative to the best substrate (Suc-AAPF-pNA) for the enzymes.

TABLE 3 pH-activity profile

| pH | *Kribbella solani* S1A protease | *Kribbella aluminosa* S1A protease | Protease 10R |
|---|---|---|---|
| 2 | 0.00 | 0.00 | |
| 3 | 0.01 | 0.01 | 0.00 |
| 4 | 0.04 | 0.05 | 0.02 |
| 5 | 0.15 | 0.19 | 0.07 |
| 6 | 0.48 | 0.49 | 0.21 |
| 7 | 0.74 | 0.72 | 0.44 |
| 8 | 0.92 | 0.93 | 0.67 |
| 9 | 0.98 | 1.00 | 0.88 |
| 10 | 1.00 | 0.97 | 1.00 |
| 11 | 0.91 | 0.90 | 0.93 |

TABLE 4 pH-stability profile (residual activity after 2 hours at 37° C.)

| pH | *Kribbella solani* S1A protease | *Kribbella aluminosa* S1A protease | Protease 10R |
|---|---|---|---|
| 2 | 0.94 | 0.82 | 0.78 |
| 3 | 1.00 | 1.04 | 1.03 |
| 4 | 0.99 | 1.00 | 0.99 |
| 5 | 1.00 | 1.06 | 1.00 |
| 6 | 1.02 | 0.98 | 1.03 |
| 7 | 0.99 | 1.00 | 1.01 |
| 8 | 0.99 | 0.97 | 0.98 |
| 9 | 0.91 | 0.98 | 0.99 |
| 10 | 0.38 | 0.97 | 0.99 |
| 11 | 0.00 | 0.92 | 0.86 |
| After 2 hours at 5° C. | 1.00 (at pH 9) | 1.00 (at pH 9) | 1.00 (at pH 9) |

TABLE 5

Temperature activity profile at pH 6.5 or pH 7

| Temp (° C.) | *Kribbella solani* S1A protease (pH 6.5) | *Kribbella aluminosa* S1A protease (pH 7) | Protease 10R (pH 6.5) |
|---|---|---|---|
| 15 | 0.00 | 0.01 | 0.01 |
| 25 | 0.02 | 0.01 | 0.02 |
| 37 | 0.04 | 0.02 | 0.06 |
| 50 | 0.14 | 0.11 | 0.13 |
| 60 | 0.39 | 0.36 | 0.35 |
| 70 | 1.00 | 1.00 | 0.96 |
| 80 | 0.40 | 0.98 | 1.00 |
| 90 | — | 0.20 | 0.18 |

TABLE 6

P1-specificity on 10 Suc-AAPX-pNA substrates at pH 9

| Suc-AAPX-pNA | *Kribbella solani* S1A protease | *Kribbella aluminosa* S1A protease | Protease 10R |
|---|---|---|---|
| Suc-AAPA-pNA | 0.13 | 0.15 | 0.13 |
| Suc-AAPR-pNA | 0.15 | 0.17 | 0.09 |
| Suc-AAPD-pNA | 0.01 | 0.00 | 0.00 |
| Suc-AAPI-pNA | 0.00 | 0.00 | 0.00 |
| Suc-AAPM-pNA | 0.35 | 0.37 | 0.78 |
| Suc-AAPV-pNA | 0.01 | 0.01 | 0.01 |
| Suc-AAPL-pNA | 0.21 | 0.19 | 0.18 |
| Suc-AAPE-pNA | 0.00 | 0.00 | 0.00 |
| Suc-AAPK-pNA | 0.08 | 0.09 | 0.08 |
| Suc-AAPF-pNA | 1.00 | 1.00 | 1.00 |

Other Characteristics for the S1A Protease from *Kribbella solani*

Inhibitor: PMSF.

The relative molecular weight as determined by SDS-PAGE was approx. $M_r$=23 k Da.

The molecular weight determined by Intact molecular weight analysis was 18900.5 Da.

The mature sequence (from MS-EDMAN data and P23BSS sequence) was as indicated in SEQ ID NO: 2:

The calculated molecular weight from this mature sequence was 18900.5 Da.

Other Characteristics for the S1A Protease from *Kribbella aluminosa*

Inhibitor: PMSF.

The relative molecular weight as determined by SDS-PAGE was approx. $M_r$=21 kDa.

The molecular weight determined by Intact molecular weight analysis was 19078.1 Da.

The mature sequence (from MS-EDMAN data and P23XDA sequence) was as indicated in SEQ ID NO: 4

The calculated molecular weight from this mature sequence was 19077.7 Da.

Example 4

Protease Activity in Soybean-Maize Meal Assay (SMM Assay)

A soybean-maize meal assay was used to describe the activity of the proteases on a substrate relevant for animal feed. The results are shown in Table 7 below. The maximum activity for each protease is set to 1.00 and the other values are represented as relative to the maximum activity. The proteases of the invention show a lower pH optimum on soybean-maize meal than 10R and a higher relative activity in the broad physiological pH range from 3-7. This indicates a possibility for the proteases of the invention to hydrolyse diet protein in the entire digestive tract of pigs and poultry. The pH in the gastrointestinal tract varies from acidic (typically pH 2-4) in the stomach of pigs and proventriculus and gizzard of poultry to pH 4-6 in the crop of poultry and pH 6-7 in the small intestine of pigs and poultry.

TABLE 7

Relative protease activity on soybean-maize meal at pH 3.0, 4.0, 5.0, 6.0 and 7.0

| pH | Kribbella solani S1A protease | Kribbella aluminosa S1A protease | Protease 10R |
|---|---|---|---|
| 3.0 | 0.55 | 0.41 | 0.08 |
| 4.0 | 0.47 | 0.53 | 0.10 |
| 5.0 | 0.82 | 0.83 | 0.24 |
| 6.0 | 1.00 | 1.00 | 0.62 |
| 7.0 | 0.76 | 0.83 | 1.00 |

Example 5

In Vitro Digestion Assay

A simulated gastro-intestinal digestion assay was performed to evaluate the potential of proteases for increasing protein digestibility in monogastric animals. The effect of the proteases was measured as an increase in protein solubilization. The results are shown in Table 8 below. The S1A protease from *K. solani* increased the amount of soluble protein in the samples indicating protein hydrolysis, however not to the same level as for protease 10R. A logical explanation for this is that the in vitro digestion incubation as designed for this study includes 4 hours incubation at pH 7 and only 1½ hour incubation at pH≤6, the pH area where the *K. solani* S1A protease of the invention has an advantage above that of protease 10R.

TABLE 8

The level of soluble protein as percent of total protein in in vitro digestion samples after treatment with *Kribbella solani* S1A protease or protease 10R

| Enzyme (mg enzyme protein/kg feed) | Soluble protein of total (%) | |
|---|---|---|
| | Average[1] | Standard deviation |
| No enzyme | 93.45[b] | 2.06 |
| *Kribbella solani* S1A protease (100) | 97.64[a] | 1.06 |
| Protease 10R (100) | 100.64[a] | 1.75 |

[1]Different superscript letters indicate significant differences (P < 0.05).

Example 6

Thermostability

An aliquot of the protein sample of protease (purified as described in Example 2) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 μm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 7

Steam Stability

Residual activity of the protease after steam treatment may be evaluated using the following assay.

In these experiments a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using e.g. the Suc-AAPF-pNA or o-Phthaldialdehyde (OPA) assay. Each enzyme sample is compared to a similar sample that had not been steam treated in order to calculate residual activity.

Example 8

Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A recombinant host cell comprising a polynucleotide encoding a polypeptide having protease activity, wherein the polypeptide has at least 85% sequence identity to the mature polypeptide of SEQ ID NO: 2 and/or SEQ ID NO: 4 and the polynucleotide is operably linked to one or more control sequences that direct the production of the polypeptide in the recombinant host cell.

2. The recombinant host cell of claim 1, wherein the polypeptide has at least 90% sequence identity to the mature polypeptide of SEQ ID NO: 2 and/or SEQ ID NO: 4.

3. The recombinant host cell of claim 1, wherein the polypeptide has at least 95% sequence identity to the mature polypeptide of SEQ ID NO: 2 and/or SEQ ID NO: 4.

4. The recombinant host cell of claim 1, wherein the polypeptide has at least 97% sequence identity to the mature polypeptide of SEQ ID NO: 2 and/or SEQ ID NO: 4.

5. The recombinant host cell of claim 1, wherein the polypeptide is encoded by a polynucleotide that hybridizes under high stringency conditions with
   (a) the mature polypeptide coding sequence of SEQ ID NO: 1 or SEQ ID NO: 3, (b) the full-length complementary strand of (i) or (ii).

6. The recombinant host cell of claim 1, wherein the polypeptide comprises or consists of SEQ ID NO: 2.

7. The recombinant host cell of claim 1, wherein the polypeptide comprises or consists of SEQ ID NO: 4.

8. The recombinant host cell of claim 1, wherein the polypeptide is a fragment of SEQ ID NO: 2 or SEQ ID NO: 4, wherein the fragment has protease activity.

9. A method of producing the polypeptide having protease activity, comprising:
   (a) cultivating a recombinant host cell of claim 1 under conditions conducive for production of the polypeptide; and
   (b) recovering the polypeptide.

10. A method of producing the polypeptide having protease activity, comprising:
    (a) cultivating a recombinant host cell of claim 2 under conditions conducive for production of the polypeptide; and
    (b) recovering the polypeptide.

11. A method of producing the polypeptide having protease activity, comprising:

(a) cultivating a recombinant host cell of claim 3 under conditions conducive for production of the polypeptide; and
(b) recovering the polypeptide.

12. A method of producing the polypeptide having protease activity, comprising:
(a) cultivating a recombinant host cell of claim 4 under conditions conducive for production of the polypeptide; and
(b) recovering the polypeptide.

13. A method of producing the polypeptide having protease activity, comprising:
(a) cultivating a recombinant host cell of claim 5 under conditions conducive for production of the polypeptide; and
(b) recovering the polypeptide.

14. A method of producing the polypeptide having protease activity, comprising:
(a) cultivating a recombinant host cell of claim 6 under conditions conducive for production of the polypeptide; and
(b) recovering the polypeptide.

15. A method of producing the polypeptide having protease activity, comprising:
(a) cultivating a recombinant host cell of claim 7 under conditions conducive for production of the polypeptide; and
(b) recovering the polypeptide.

16. A method of producing the polypeptide having protease activity, comprising:
(a) cultivating a recombinant host cell of claim 8 under conditions conducive for production of the polypeptide; and
(b) recovering the polypeptide.

17. The method of claim 9, wherein the recombinant host cell is a Bacillus recombinant host cell.

18. The method of claim 10, wherein the recombinant host cell is a Bacillus recombinant host cell.

19. The method of claim 11, wherein the recombinant host cell is a Bacillus recombinant host cell.

20. The method of claim 12, wherein the recombinant host cell is a Bacillus recombinant host cell.

* * * * *

SEQUENCE LISTING

```
<160> NUMBER OF SEQ ID NOS: 17

<210> SEQ ID NO 1
<211> LENGTH: 879
<212> TYPE: DNA
<213> ORGANISM: Kribbella solani
<220> FEATURE:
<221> NAME/KEY: CDS
<222> LOCATION: (1)..(879)
<220> FEATURE:
<221> NAME/KEY: sig_peptide
<222> LOCATION: (1)..(90)
<220> FEATURE:
<221> NAME/KEY: mat_peptide
<222> LOCATION: (316)..(879)

<400> SEQUENCE: 1 atg  aaa  ctg  tcc  cca  ttc  cgc  cgc  acc  acc  gca  atc  ctg  gcc  gcg  gcc         48
Met  Lys  Leu  Ser  Pro  Phe  Arg  Arg  Thr  Thr  Ala  Ile  Leu  Ala  Ala  Ala
-105                 -100                 -95                  -90 ggg  ctt  gcc  gcc  gcc  gga  ctg  ctg  gcg  tcg  caa  gcc  tcg  gcc  gca  ccg         96
Gly  Leu  Ala  Ala  Ala  Gly  Leu  Leu  Ala  Ser  Gln  Ala  Ser  Ala  Ala  Pro
             -85                  -80                  -75 gtg  aac  ccg  tcc  gcg  ctg  tcc  gcc  tcg  gcg  atc  acg  tcg  acg  ctg  agc        144
Val  Asn  Pro  Ser  Ala  Leu  Ser  Ala  Ser  Ala  Ile  Thr  Ser  Thr  Leu  Ser
        -70                  -65                  -60 aag  gac  gcg  acc  atc  ccc  ggt  acg  gcg  tgg  cag  acc  gct  ccg  gac  ggc        192
Lys  Asp  Ala  Thr  Ile  Pro  Gly  Thr  Ala  Trp  Gln  Thr  Ala  Pro  Asp  Gly
   -55                  -50                  -45 cgg  atc  atc  gtg  tcg  tac  gac  gac  acc  gtg  acc  ggc  gcg  aag  ctg  tcc        240
Arg  Ile  Ile  Val  Ser  Tyr  Asp  Asp  Thr  Val  Thr  Gly  Ala  Lys  Leu  Ser
 -40                  -35                  -30 aag  ctg  acc  agt  gtg  acc  aag  cag  ttc  ggc  cag  cgg  atc  acg  ctg  gag        288
Lys  Leu  Thr  Ser  Val  Thr  Lys  Gln  Phe  Gly  Gln  Arg  Ile  Thr  Leu  Glu
-25                  -20                  -15                  -10 aag  atg  aag  ggc  aag  ctg  acc  aag  tac  atc  gcc  ggc  ggc  gac  gcc  atc        336
Lys  Met  Lys  Gly  Lys  Leu  Thr  Lys  Tyr  Ile  Ala  Gly  Gly  Asp  Ala  Ile
              -5                   -1   1                    5 tac  ggc  ggt  cag  tac  cgg  tgc  tcg  ctc  ggc  ttc  aac  gtc  cgc  agc  ggc        384
Tyr  Gly  Gly  Gln  Tyr  Arg  Cys  Ser  Leu  Gly  Phe  Asn  Val  Arg  Ser  Gly
              10                   15                   20 agc  acg  tac  tac  ttc  ctg  acc  gcg  ggt  cac  tgc  ggc  aac  atc  gcc  tcc        432
Ser  Thr  Tyr  Tyr  Phe  Leu  Thr  Ala  Gly  His  Cys  Gly  Asn  Ile  Ala  Ser
         25                   30                   35 agc  tgg  tac  gcg  aac  tcc  gcc  aag  acc  acg  ctc  ctc  ggt  acg  acg  tac        480
Ser  Trp  Tyr  Ala  Asn  Ser  Ala  Lys  Thr  Thr  Leu  Leu  Gly  Thr  Thr  Tyr
```

```
                40                  45                  50                  55
gga tcg agc ttc ccc ggc aac gac tac gcg atc gtg cag tac agc tcc        528
Gly Ser Ser Phe Pro Gly Asn Asp Tyr Ala Ile Val Gln Tyr Ser Ser
                60                  65                  70 tcg tac aca aac cac ccc ggc acg gtc gac ctg tac aac ggc tcc tcg        576
Ser Tyr Thr Asn His Pro Gly Thr Val Asp Leu Tyr Asn Gly Ser Ser
            75                  80                  85 cag gac atc acg tcc gcc ggc aac gcg act gtt ggt cag gcg gtc aag        624
Gln Asp Ile Thr Ser Ala Gly Asn Ala Thr Val Gly Gln Ala Val Lys
        90                  95                 100 cgc agt ggt agc acc acc ggc gtc cac agc ggc agt gtc acc ggg ctg        672
Arg Ser Gly Ser Thr Thr Gly Val His Ser Gly Ser Val Thr Gly Leu
    105                 110                 115 aac gcc acc gtg aac tac gcc gaa ggc acc gtc acc ggc ctg atc cgc        720
Asn Ala Thr Val Asn Tyr Ala Glu Gly Thr Val Thr Gly Leu Ile Arg
120                 125                 130                 135 acc aac gtc tgc gcc gaa ggc ggc gac tcc ggc ggc gcc ctc ttc gcc        768
Thr Asn Val Cys Ala Glu Gly Gly Asp Ser Gly Gly Ala Leu Phe Ala
                140                 145                 150 ggc acc gta gcc ctc ggc ctg acc tcc ggc ggc tcc ggc aac tgc tcc        816
Gly Thr Val Ala Leu Gly Leu Thr Ser Gly Gly Ser Gly Asn Cys Ser
            155                 160                 165 tcc ggc ggc acc acc tac ttc cag ccc gtc acc gaa gtc ctc tcc cgc        864
Ser Gly Gly Thr Thr Tyr Phe Gln Pro Val Thr Glu Val Leu Ser Arg
        170                 175                 180 tac ggc gtc agc gtc                                                    879
Tyr Gly Val Ser Val
    185

<210> SEQ ID NO 2
<211> LENGTH: 293
<212> TYPE: PRT
<213> ORGANISM: Kribbella solani

<400> SEQUENCE: 2

Met  Lys Leu Ser Pro Phe  Arg Arg Thr Thr Ala Ile Leu Ala Ala Ala
-105                -100                 -95                 -90

Gly Leu Ala Ala Ala Gly Leu Leu Ala Ser Gln Ala Ser Ala Ala Pro
            -85                 -80                 -75

Val Asn Pro Ser Ala Leu Ser Ala Ser Ala Ile Thr Ser Thr Leu Ser
        -70                 -65                 -60

Lys Asp Ala Thr Ile Pro Gly Thr Ala Trp Gln Thr Ala Pro Asp Gly
    -55                 -50                 -45

Arg Ile Ile Val Ser Tyr Asp Asp Thr Val Thr Gly Ala Lys Leu Ser
-40                 -35                 -30

Lys Leu Thr Ser Val Thr Lys Gln Phe Gly Gln Arg Ile Thr Leu Glu
-25                 -20                 -15                 -10

Lys Met Lys Gly Lys Leu Thr Lys Tyr Ile Ala Gly Gly Asp Ala Ile
            -5                  -1  1                   5

Tyr Gly Gly Gln Tyr Arg Cys Ser Leu Gly Phe Asn Val Arg Ser Gly
        10                  15                  20

Ser Thr Tyr Tyr Phe Leu Thr Ala Gly His Cys Gly Asn Ile Ala Ser
    25                  30                  35

Ser Trp Tyr Ala Asn Ser Ala Lys Thr Thr Leu Leu Gly Thr Thr Tyr
40                  45                  50                  55

Gly Ser Ser Phe Pro Gly Asn Asp Tyr Ala Ile Val Gln Tyr Ser Ser
            60                  65                  70
```

```
Ser Tyr Thr Asn His Pro Gly Thr Val Asp Leu Tyr Asn Gly Ser Ser
         75                  80                  85

Gln Asp Ile Thr Ser Ala Gly Asn Ala Thr Val Gly Gln Ala Val Lys
     90                  95                 100

Arg Ser Gly Ser Thr Thr Gly Val His Ser Gly Ser Val Thr Gly Leu
105                 110                 115

Asn Ala Thr Val Asn Tyr Ala Glu Gly Thr Val Thr Gly Leu Ile Arg
120                 125                 130                 135

Thr Asn Val Cys Ala Glu Gly Gly Asp Ser Gly Gly Ala Leu Phe Ala
                140                 145                 150

Gly Thr Val Ala Leu Gly Leu Thr Ser Gly Gly Ser Gly Asn Cys Ser
            155                 160                 165

Ser Gly Gly Thr Thr Tyr Phe Gln Pro Val Thr Glu Val Leu Ser Arg
        170                 175                 180

Tyr Gly Val Ser Val
        185

<210> SEQ ID NO 3
<211> LENGTH: 882
<212> TYPE: DNA
<213> ORGANISM: Kribbella aluminosa
<220> FEATURE:
<221> NAME/KEY: CDS
<222> LOCATION: (1)..(882)
<220> FEATURE:
<221> NAME/KEY: sig_peptide
<222> LOCATION: (1)..(90)
<220> FEATURE:
<221> NAME/KEY: mat_peptide
<222> LOCATION: (316)..(882)

<400> SEQUENCE: 3 atg aac atg tcc ccg ttc cgc cgt acc ctc gct gtc ctg gcc gcg gcc      48
Met Asn Met Ser Pro Phe Arg Arg Thr Leu Ala Val Leu Ala Ala Ala
-105                -100                 -95                 -90 ggg ctt gct gcc agc gga ctg ctg gcg acg cag gcc tcg gcc gca ccg      96
Gly Leu Ala Ala Ser Gly Leu Leu Ala Thr Gln Ala Ser Ala Ala Pro
             -85                 -80                 -75 gtc gac ccg tcc acc ctg tcg gcc gcc gcg atc acg tcc acc ctg agc     144
Val Asp Pro Ser Thr Leu Ser Ala Ala Ala Ile Thr Ser Thr Leu Ser
        -70                 -65                 -60 gag aac gcg acg atc ccc ggt acg gcg tgg gag acc ggc cct gac ggc     192
Glu Asn Ala Thr Ile Pro Gly Thr Ala Trp Glu Thr Gly Pro Asp Gly
    -55                 -50                 -45 cgg atc atc gtg tcg tac gac gag acc gtc acc ggt gcc aag ctg gcg     240
Arg Ile Ile Val Ser Tyr Asp Glu Thr Val Thr Gly Ala Lys Leu Ala
-40                 -35                 -30 aag ctg acc agc gtg acg aag cag ttc ggc aag cgg atc aag ctc gag     288
Lys Leu Thr Ser Val Thr Lys Gln Phe Gly Lys Arg Ile Lys Leu Glu
-25                 -20                 -15                 -10 aag atg tcc ggc aag ctg acg aag tac atc gcc ggc ggc gac gcc atc     336
Lys Met Ser Gly Lys Leu Thr Lys Tyr Ile Ala Gly Gly Asp Ala Ile
            -5                  -1  1                   5 tac ggc ggg cag tac cgc tgc tcg ctc ggc ttc aac gtg cgc agc ggc     384
Tyr Gly Gly Gln Tyr Arg Cys Ser Leu Gly Phe Asn Val Arg Ser Gly
        10                  15                  20 agc acc tac tac ttc ctg acc gcg ggc cac tgc ggg aac atc gcg tcc     432
Ser Thr Tyr Tyr Phe Leu Thr Ala Gly His Cys Gly Asn Ile Ala Ser
    25                  30                  35 agc tgg tac gcg aac tcc agc aag acc acg ctg ctc ggc acc gtc gcc     480
Ser Trp Tyr Ala Asn Ser Ser Lys Thr Thr Leu Leu Gly Thr Val Ala
```

```
             40                  45                  50                  55
ggt tca agc ttc ccc ggc aac gac tac gcc atc gtc agg tac agc acg       528
Gly Ser Ser Phe Pro Gly Asn Asp Tyr Ala Ile Val Arg Tyr Ser Thr
                60                  65                  70 tcg tac acc aac cac ccg ggc acc gtg aac ctc tac aac ggt tcg tcc       576
Ser Tyr Thr Asn His Pro Gly Thr Val Asn Leu Tyr Asn Gly Ser Ser
            75                  80                  85 cag gac atc acg tcc gcc ggc aac gcc tac gtg ggc cag gcg gtc aag       624
Gln Asp Ile Thr Ser Ala Gly Asn Ala Tyr Val Gly Gln Ala Val Lys
        90                  95                 100 cgc agt ggt agc acg acc ggt gtg cac agc ggc tcg gtc acc gcg acc       672
Arg Ser Gly Ser Thr Thr Gly Val His Ser Gly Ser Val Thr Ala Thr
    105                 110                 115 aac gcc acg gtc aac tac gcc gaa ggc acc gtc acc ggc ctg atc cgc       720
Asn Ala Thr Val Asn Tyr Ala Glu Gly Thr Val Thr Gly Leu Ile Arg
120                 125                 130                 135 acc aca gtc tgc gcc gaa ggc ggc gac tcc ggc ggc gcc ctg ttc gcc       768
Thr Thr Val Cys Ala Glu Gly Gly Asp Ser Gly Gly Ala Leu Phe Ala
                140                 145                 150 ggc acc gta gcc ctc ggc ctg acc tcc ggc ggc tcc ggc aac tgc tca       816
Gly Thr Val Ala Leu Gly Leu Thr Ser Gly Gly Ser Gly Asn Cys Ser
            155                 160                 165 tcc ggc ggc acc acc tac ttc cag ccc gtc acc gaa gtc ctc tcc cgc       864
Ser Gly Gly Thr Thr Tyr Phe Gln Pro Val Thr Glu Val Leu Ser Arg
        170                 175                 180 tac ggc gtg agc gtc tac                                               882
Tyr Gly Val Ser Val Tyr
    185

<210> SEQ ID NO 4
<211> LENGTH: 294
<212> TYPE: PRT
<213> ORGANISM: Kribbella aluminosa

<400> SEQUENCE: 4

Met  Asn Met Ser Pro Phe  Arg Arg Thr Leu Ala  Val Leu Ala Ala Ala
-105                -100                 -95                  -90

Gly Leu Ala Ala Ser Gly Leu Leu Ala Thr Gln Ala Ser Ala Ala Pro
            -85                 -80                 -75

Val Asp Pro Ser Thr Leu Ser Ala Ala Ile Thr Ser Thr Leu Ser
        -70                 -65                 -60

Glu Asn Ala Thr Ile Pro Gly Thr Ala Trp Glu Thr Gly Pro Asp Gly
        -55                 -50                 -45

Arg Ile Ile Val Ser Tyr Asp Glu Thr Val Thr Gly Ala Lys Leu Ala
    -40                 -35                 -30

Lys Leu Thr Ser Val Thr Lys Gln Phe Gly Lys Arg Ile Lys Leu Glu
-25                 -20                 -15                 -10

Lys Met Ser Gly Lys Leu Thr Lys Tyr Ile Ala Gly Gly Asp Ala Ile
        -5                  -1  1                   5

Tyr Gly Gly Gln Tyr Arg Cys Ser Leu Gly Phe Asn Val Arg Ser Gly
            10                  15                  20

Ser Thr Tyr Tyr Phe Leu Thr Ala Gly His Cys Gly Asn Ile Ala Ser
    25                  30                  35

Ser Trp Tyr Ala Asn Ser Ser Lys Thr Thr Leu Leu Gly Thr Val Ala
40                  45                  50                  55

Gly Ser Ser Phe Pro Gly Asn Asp Tyr Ala Ile Val Arg Tyr Ser Thr
                60                  65                  70
```

```
Ser Tyr Thr Asn His Pro Gly Thr Val Asn Leu Tyr Asn Gly Ser Ser
             75                  80                  85

Gln Asp Ile Thr Ser Ala Gly Asn Ala Tyr Val Gly Gln Ala Val Lys
         90                  95                 100

Arg Ser Gly Ser Thr Thr Gly Val His Ser Gly Ser Val Thr Ala Thr
    105                 110                 115

Asn Ala Thr Val Asn Tyr Ala Glu Gly Thr Val Thr Gly Leu Ile Arg
120                 125                 130                 135

Thr Thr Val Cys Ala Glu Gly Gly Asp Ser Gly Gly Ala Leu Phe Ala
             140                 145                 150

Gly Thr Val Ala Leu Gly Leu Thr Ser Gly Gly Ser Gly Asn Cys Ser
         155                 160                 165

Ser Gly Gly Thr Thr Tyr Phe Gln Pro Val Thr Glu Val Leu Ser Arg
    170                 175                 180

Tyr Gly Val Ser Val Tyr
    185

<210> SEQ ID NO 5
<211> LENGTH: 888
<212> TYPE: DNA
<213> ORGANISM: Kribbella flavida
<220> FEATURE:
<221> NAME/KEY: CDS
<222> LOCATION: (1)..(888)
<220> FEATURE:
<221> NAME/KEY: sig_peptide
<222> LOCATION: (1)..(84)
<220> FEATURE:
<221> NAME/KEY: mat_peptide
<222> LOCATION: (319)..(888)

<400> SEQUENCE: 5 atg cgt att cgc cgt gcc gtg gcc ctg ctg gca acc gcc ggt ctg gcc      48
Met Arg Ile Arg Arg Ala Val Ala Leu Leu Ala Thr Ala Gly Leu Ala
-105                -100                 -95 acc acc acc gtt cag ctc gca gcc ccg gcc aac gcg gcc ccg ggt ggc      96
Thr Thr Thr Val Gln Leu Ala Ala Pro Ala Asn Ala Ala Pro Gly Gly
 -90                 -85                 -80                 -75 gag gca ccc gcc gtc acc tcg gcg agc agc atc acc gcc acc ctg gcc     144
Glu Ala Pro Ala Val Thr Ser Ala Ser Ser Ile Thr Ala Thr Leu Ala
             -70                 -65                 -60 aag gag gcg tcg atc ccg ggc acc gcc tgg atg acc gac gag aag tcc     192
Lys Glu Ala Ser Ile Pro Gly Thr Ala Trp Met Thr Asp Glu Lys Ser
         -55                 -50                 -45 ggc cgc atc atc gtc tcg tac gac gac acc gtg agc ggc ggc aag ttc     240
Gly Arg Ile Ile Val Ser Tyr Asp Asp Thr Val Ser Gly Gly Lys Phe
    -40                 -35                 -30 gcc gct ctc acc gcc gtc acc aag cgc ttc ggc agc cag gtc gtg ctg     288
Ala Ala Leu Thr Ala Val Thr Lys Arg Phe Gly Ser Gln Val Val Leu
-25                 -20                 -15 gag aag ctg ccc ggc gta ctc agc aag cgg atc agc ggc gga cag gcc     336
Glu Lys Leu Pro Gly Val Leu Ser Lys Arg Ile Ser Gly Gly Gln Ala
-10                  -5                  -1   1               5 atc tac ggt ggc ggc tac cgc tgc tcg ctc ggc ttc aac gtc cgc gac     384
Ile Tyr Gly Gly Gly Tyr Arg Cys Ser Leu Gly Phe Asn Val Arg Asp
             10                  15                  20 agc gcc ggc acc tac tac ttc atc acc gcc ggc cac tgc acc aac tcg     432
Ser Ala Gly Thr Tyr Tyr Phe Ile Thr Ala Gly His Cys Thr Asn Ser
         25                  30                  35 gcc agc acc tgg tac gcc aac tcg tcg cag tcc acc gtg ctc ggc acc     480
Ala Ser Thr Trp Tyr Ala Asn Ser Ser Gln Ser Thr Val Leu Gly Thr
```

```
                    40                  45                  50
cgg acc ggc agc agc ttc ccg ggc aac gac tac ggc atc gtc cgg tac        528
Arg Thr Gly Ser Ser Phe Pro Gly Asn Asp Tyr Gly Ile Val Arg Tyr
 55                  60                  65                  70 agc acg tcg tac acg aac cac ccc ggc aac gtg tac ctc tac aac ggc        576
Ser Thr Ser Tyr Thr Asn His Pro Gly Asn Val Tyr Leu Tyr Asn Gly
                 75                  80                  85 tcg tac cag gac atc acc acg gcg ggc aac gcg tcc gtc ggc cag gcc        624
Ser Tyr Gln Asp Ile Thr Thr Ala Gly Asn Ala Ser Val Gly Gln Ala
             90                  95                 100 gtg cgc cgc agc ggc agc acc acc ggt ctg cgc agc ggc tcg gtc acc        672
Val Arg Arg Ser Gly Ser Thr Thr Gly Leu Arg Ser Gly Ser Val Thr
        105                 110                 115 ggc gtc aac gcg acg gtg aac tac ccc gag ggc tcc gtc agc ggc ctg        720
Gly Val Asn Ala Thr Val Asn Tyr Pro Glu Gly Ser Val Ser Gly Leu
    120                 125                 130 atc cgc acc aac gtc tgc gcc gaa ggc ggc gac tcc ggc ggc tca ctg        768
Ile Arg Thr Asn Val Cys Ala Glu Gly Gly Asp Ser Gly Gly Ser Leu
135                 140                 145                 150 ttc gcc ggc tcc acc gcc ctg ggt ctg acc tcc ggc ggc agc ggc aac        816
Phe Ala Gly Ser Thr Ala Leu Gly Leu Thr Ser Gly Gly Ser Gly Asn
                155                 160                 165 tgc tcc acc ggc ggc acg acc tac ttc cag ccc gtc atc gag gtc ctc        864
Cys Ser Thr Gly Gly Thr Thr Tyr Phe Gln Pro Val Ile Glu Val Leu
            170                 175                 180 aac cgc tac ggc gtc aac gtc tac                                        888
Asn Arg Tyr Gly Val Asn Val Tyr
        185                 190

<210> SEQ ID NO 6
<211> LENGTH: 296
<212> TYPE: PRT
<213> ORGANISM: Kribbella flavida

<400> SEQUENCE: 6

Met Arg  Ile Arg Arg Ala Val  Ala Leu Leu Ala Thr Ala Gly Leu Ala
    -105                -100                 -95

Thr Thr Thr Val Gln Leu Ala Ala Pro Ala Asn Ala Ala Pro Gly Gly
-90                  -85                 -80                 -75

Glu Ala Pro Ala Val Thr Ser Ala Ser Ser Ile Thr Ala Thr Leu Ala
                -70                 -65                 -60

Lys Glu Ala Ser Ile Pro Gly Thr Ala Trp Met Thr Asp Glu Lys Ser
            -55                 -50                 -45

Gly Arg Ile Ile Val Ser Tyr Asp Asp Thr Val Ser Gly Gly Lys Phe
        -40                 -35                 -30

Ala Ala Leu Thr Ala Val Thr Lys Arg Phe Gly Ser Gln Val Val Leu
    -25                 -20                 -15

Glu Lys Leu Pro Gly Val Leu Ser Lys Arg Ile Ser Gly Gly Gln Ala
-10                  -5                  -1  1                  5

Ile Tyr Gly Gly Gly Tyr Arg Cys Ser Leu Gly Phe Asn Val Arg Asp
                10                  15                  20

Ser Ala Gly Thr Tyr Tyr Phe Ile Thr Ala Gly His Cys Thr Asn Ser
            25                  30                  35

Ala Ser Thr Trp Tyr Ala Asn Ser Ser Gln Ser Thr Val Leu Gly Thr
        40                  45                  50

Arg Thr Gly Ser Ser Phe Pro Gly Asn Asp Tyr Gly Ile Val Arg Tyr
 55                  60                  65                  70
```

```
Ser Thr Ser Tyr Thr Asn His Pro Gly Asn Val Tyr Leu Tyr Asn Gly
             75                  80                  85

Ser Tyr Gln Asp Ile Thr Thr Ala Gly Asn Ala Ser Val Gly Gln Ala
         90                  95                 100

Val Arg Arg Ser Gly Ser Thr Thr Gly Leu Arg Ser Gly Ser Val Thr
        105                 110                 115

Gly Val Asn Ala Thr Val Asn Tyr Pro Glu Gly Ser Val Ser Gly Leu
    120                 125                 130

Ile Arg Thr Asn Val Cys Ala Glu Gly Gly Asp Ser Gly Gly Ser Leu
135                 140                 145                 150

Phe Ala Gly Ser Thr Ala Leu Gly Leu Thr Ser Gly Gly Ser Gly Asn
                155                 160                 165

Cys Ser Thr Gly Gly Thr Thr Tyr Phe Gln Pro Val Ile Glu Val Leu
            170                 175                 180

Asn Arg Tyr Gly Val Asn Val Tyr
            185                 190

<210> SEQ ID NO 7
<211> LENGTH: 1473
<212> TYPE: DNA
<213> ORGANISM: Nocardiopsis sp.
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 7
acgtttggta cgggtaccgg tgtccgcatg tggccagaat gcccccttgc dacagggaac     60
ggattcggtc ggtagcgcat cgactccgac aaccgcgagg tggccgttcg cgtcgccacg    120
ttctgcgacc gtcatgcgac ccatcatcgg gtgaccccac cgagctctga atggtccacc    180
gttctgacgg tctttccctc accaaaacgt gcacctatgg ttaggacgtt gtttaccgaa    240
tgtctcggtg aacgacaggg gccggacggt attcggcccc gatcccccgt tgatcccccc    300
aggagagtag ggacccc atg cga ccc tcc ccc gtt gtc tcc gcc atc ggt       350
                   Met Arg Pro Ser Pro Val Val Ser Ala Ile Gly
                      -190                -185 acg gga gcg ctg gcc ttc ggt ctg gcg ctg tcc ggt acc ccg ggt           395
Thr Gly Ala Leu Ala Phe Gly Leu Ala Leu Ser Gly Thr Pro Gly
       -180                -175                -170 gcc ctc gcg gcc acc gga gcg ctc ccc cag tca ccc acc ccg gag           440
Ala Leu Ala Ala Thr Gly Ala Leu Pro Gln Ser Pro Thr Pro Glu
   -165                -160                -155 gcc gac gcg gtc tcc atg cag gag gcg ctc cag cgc gac ctc gac           485
Ala Asp Ala Val Ser Met Gln Glu Ala Leu Gln Arg Asp Leu Asp
   -150                -145                -140 ctg acc tcc gcc gag gcc gag gag ctg ctg gcc gcc cag gac acc           530
Leu Thr Ser Ala Glu Ala Glu Glu Leu Leu Ala Ala Gln Asp Thr
   -135                -130                -125 gcc ttc gag gtc gac gag gcc gcg gcc gag gcc gcc ggg gac gcc           575
Ala Phe Glu Val Asp Glu Ala Ala Ala Glu Ala Ala Gly Asp Ala
   -120                -115                -110 tac ggc ggc tcc gtc ttc gac acc gag agc ctg gaa ctg acc gtc ctg       623
Tyr Gly Gly Ser Val Phe Asp Thr Glu Ser Leu Glu Leu Thr Val Leu
       -105                -100                -95
```

```
gtc acc gat gcc gcc gcg gtc gag gcc gtg gag gcc acc ggc gcc ggg       671
Val Thr Asp Ala Ala Ala Val Glu Ala Val Glu Ala Thr Gly Ala Gly
        -90             -85                 -80 acc gag ctg gtc tcc tac ggc atc gac ggt ctc gac gag atc gtc cag       719
Thr Glu Leu Val Ser Tyr Gly Ile Asp Gly Leu Asp Glu Ile Val Gln
    -75                 -70                 -65 gag ctc aac gcc gcc gac gcc gtt ccc ggt gtg gtc ggc tgg tac ccg       767
Glu Leu Asn Ala Ala Asp Ala Val Pro Gly Val Val Gly Trp Tyr Pro
-60                 -55                 -50                 -45 gac gtg gcg ggt gac acc gtc gtc ctg gag gtc ctg gag ggt tcc gga       815
Asp Val Ala Gly Asp Thr Val Val Leu Glu Val Leu Glu Gly Ser Gly
                -40                 -35                 -30 gcc gac gtc agc ggc ctg ctc gcg gac gcc ggc gtg gac gcc tcg gcc       863
Ala Asp Val Ser Gly Leu Leu Ala Asp Ala Gly Val Asp Ala Ser Ala
            -25                 -20                 -15 gtc gag gtg acc acg agc gac cag ccc gag ctc tac gcc gac atc atc       911
Val Glu Val Thr Thr Ser Asp Gln Pro Glu Leu Tyr Ala Asp Ile Ile
        -10                 -5              -1   1 ggt ggt ctg gcc tac acc atg ggc ggc cgc tgt tcg gtc ggc ttc gcg       959
Gly Gly Leu Ala Tyr Thr Met Gly Gly Arg Cys Ser Val Gly Phe Ala
5               10                  15                  20 gcc acc aac gcc gcc ggt cag ccc ggg ttc gtc acc gcc ggt cac tgc      1007
Ala Thr Asn Ala Ala Gly Gln Pro Gly Phe Val Thr Ala Gly His Cys
                25                  30                  35 ggc cgc gtg ggc acc cag gtg acc atc ggc aac ggc agg ggc gtc ttc      1055
Gly Arg Val Gly Thr Gln Val Thr Ile Gly Asn Gly Arg Gly Val Phe
            40                  45                  50 gag cag tcc gtc ttc ccc ggc aac gac gcg gcc ttc gtc cgc ggt acg      1103
Glu Gln Ser Val Phe Pro Gly Asn Asp Ala Ala Phe Val Arg Gly Thr
        55                  60                  65 tcc aac ttc acg ctg acc aac ctg gtc agc cgc tac aac acc ggc ggg      1151
Ser Asn Phe Thr Leu Thr Asn Leu Val Ser Arg Tyr Asn Thr Gly Gly
    70                  75                  80 tac gcc acg gtc gcc ggt cac aac cag gcc ccc atc ggc tcc tcc gtc      1199
Tyr Ala Thr Val Ala Gly His Asn Gln Ala Pro Ile Gly Ser Ser Val
85                  90                  95                  100 tgc cgc tcc ggc tcc acc acc ggt tgg cac tgc ggc acc atc cag gcc      1247
Cys Arg Ser Gly Ser Thr Thr Gly Trp His Cys Gly Thr Ile Gln Ala
                105                 110                 115 cgc ggc cag tcg gtg agc tac ccc gag ggc acc gtc acc aac atg acc      1295
Arg Gly Gln Ser Val Ser Tyr Pro Glu Gly Thr Val Thr Asn Met Thr
            120                 125                 130 cgg acc acc gtg tgc gcc gag ccc ggc gac tcc ggc tcc tac atc         1343
Arg Thr Thr Val Cys Ala Glu Pro Gly Asp Ser Gly Ser Tyr Ile
        135                 140                 145 tcc ggc acc cag gcc cag ggc gtg acc tcc ggc tcc ggc aac tgc         1391
Ser Gly Thr Gln Ala Gln Gly Val Thr Ser Gly Ser Gly Asn Cys
    150                 155                 160 cgc acc ggg ggg acc acc ttc tac cag gag gtc acc ccc atg gtg aac      1439
Arg Thr Gly Gly Thr Thr Phe Tyr Gln Glu Val Thr Pro Met Val Asn
165                 170                 175                 180 tcc tgg ggc gtc cgt ctc cgg acc tgatccccgc                           1473
Ser Trp Gly Val Arg Leu Arg Thr
                185
```

<210> SEQ ID NO 8
<211> LENGTH: 382
<212> TYPE: PRT
<213> ORGANISM: Nocardiopsis sp.

<400> SEQUENCE: 8

```
Met Arg Pro Ser Pro Val Val Ser Ala Ile Gly Thr Gly Ala Leu
            -190            -185            -180

Ala Phe Gly Leu Ala Leu Ser Gly Thr Pro Gly Ala Leu Ala Ala
            -175            -170            -165

Thr Gly Ala Leu Pro Gln Ser Pro Thr Pro Glu Ala Asp Ala Val
            -160            -155            -150

Ser Met Gln Glu Ala Leu Gln Arg Asp Leu Asp Leu Thr Ser Ala
            -145            -140            -135

Glu Ala Glu Glu Leu Leu Ala Ala Gln Asp Thr Ala Phe Glu Val
            -130            -125            -120

Asp Glu Ala Ala Ala Glu Ala Ala Gly Asp Ala Tyr Gly Gly Ser
            -115            -110            -105

Val Phe Asp Thr Glu Ser Leu Glu Leu Thr Val Leu Val Thr Asp Ala
            -100            -95             -90

Ala Ala Val Glu Ala Val Glu Ala Thr Gly Ala Gly Thr Glu Leu Val
            -85             -80             -75

Ser Tyr Gly Ile Asp Gly Leu Asp Glu Ile Val Gln Glu Leu Asn Ala
            -70             -65             -60

Ala Asp Ala Val Pro Gly Val Val Gly Trp Tyr Pro Asp Val Ala Gly
    -55             -50             -45

Asp Thr Val Val Leu Glu Val Leu Glu Gly Ser Gly Ala Asp Val Ser
-40             -35             -30             -25

Gly Leu Leu Ala Asp Ala Gly Val Asp Ala Ser Ala Val Glu Val Thr
            -20             -15             -10

Thr Ser Asp Gln Pro Glu Leu Tyr Ala Asp Ile Ile Gly Gly Leu Ala
            -5              -1  1           5

Tyr Thr Met Gly Gly Arg Cys Ser Val Gly Phe Ala Ala Thr Asn Ala
            10              15              20

Ala Gly Gln Pro Gly Phe Val Thr Ala Gly His Cys Gly Arg Val Gly
25              30              35              40

Thr Gln Val Thr Ile Gly Asn Gly Arg Gly Val Phe Glu Gln Ser Val
                45              50              55

Phe Pro Gly Asn Asp Ala Ala Phe Val Arg Gly Thr Ser Asn Phe Thr
                60              65              70

Leu Thr Asn Leu Val Ser Arg Tyr Asn Thr Gly Gly Tyr Ala Thr Val
                75              80              85

Ala Gly His Asn Gln Ala Pro Ile Gly Ser Ser Val Cys Arg Ser Gly
                90              95              100

Ser Thr Thr Gly Trp His Cys Gly Thr Ile Gln Ala Arg Gly Gln Ser
105             110             115             120

Val Ser Tyr Pro Glu Gly Thr Val Thr Asn Met Thr Arg Thr Thr Val
                125             130             135

Cys Ala Glu Pro Gly Asp Ser Gly Ser Tyr Ile Ser Gly Thr Gln
                140             145             150

Ala Gln Gly Val Thr Ser Gly Ser Gly Asn Cys Arg Thr Gly Gly
                155             160             165

Thr Thr Phe Tyr Gln Glu Val Thr Pro Met Val Asn Ser Trp Gly Val
                170             175             180

Arg Leu Arg Thr
185

<210> SEQ ID NO 9
<211> LENGTH: 47
```

```
<212> TYPE: DNA
<213> ORGANISM: Artificial sequence
<220> FEATURE:
<223> OTHER INFORMATION: Synthetic construct
<220> FEATURE:
<221> NAME/KEY: primer
<222> LOCATION: (1)..(47)

<400> SEQUENCE: 9
cttttagttc atcgatcgca tcggctgcac cggtgaaccc gtccgcg         47

<210> SEQ ID NO 10
<211> LENGTH: 51
<212> TYPE: DNA
<213> ORGANISM: Artificial sequence
<220> FEATURE:
<223> OTHER INFORMATION: Synthetic construct
<220> FEATURE:
<221> NAME/KEY: Primer
<222> LOCATION: (1)..(51)

<400> SEQUENCE: 10
gggccaaggc cggttttttta tgttttagac gctgacgccg tagcgggaga g    51

<210> SEQ ID NO 11
<211> LENGTH: 44
<212> TYPE: DNA
<213> ORGANISM: Artificial sequence
<220> FEATURE:
<223> OTHER INFORMATION: Synthetic construct
<220> FEATURE:
<221> NAME/KEY: Primer
<222> LOCATION: (1)..(44)

<400> SEQUENCE: 11
cttttagttc atcgatcgca tcggctgcac cggtcgaccc gtcc            44

<210> SEQ ID NO 12
<211> LENGTH: 41
<212> TYPE: DNA
<213> ORGANISM: Artifcial sequence
<220> FEATURE:
<221> NAME/KEY: Primer
<222> LOCATION: (1)..(41)

<400> SEQUENCE: 12
ccaaggccgg tttttttatgt ttcagtagac gctcacgccg t              41

<210> SEQ ID NO 13
<211> LENGTH: 21
<212> TYPE: DNA
<213> ORGANISM: Artificial sequence
<220> FEATURE:
<223> OTHER INFORMATION: Synthetic construct
<220> FEATURE:
<221> NAME/KEY: Primer
<222> LOCATION: (1)..(21)

<400> SEQUENCE: 13
gagtatcgcc agtaaggggc g                                     21

<210> SEQ ID NO 14
<211> LENGTH: 22
<212> TYPE: DNA
<213> ORGANISM: Artificial sequence
<220> FEATURE:
<223> OTHER INFORMATION: Synthetic construct
<220> FEATURE:
<221> NAME/KEY: Primer
```

```
<222> LOCATION: (1)..(22)

<400> SEQUENCE: 14
agccgatgcg atcgatgaac ta                                             22

<210> SEQ ID NO 15
<211> LENGTH: 25
<212> TYPE: DNA
<213> ORGANISM: Artificial sequence
<220> FEATURE:
<223> OTHER INFORMATION: Synthetic construct
<220> FEATURE:
<221> NAME/KEY: Primer
<222> LOCATION: (1)..(25)

<400> SEQUENCE: 15
taaaacataa aaaccggcc ttggc                                           25

<210> SEQ ID NO 16
<211> LENGTH: 23
<212> TYPE: DNA
<213> ORGANISM: Artificial sequence
<220> FEATURE:
<223> OTHER INFORMATION: Synthetic construct
<220> FEATURE:
<221> NAME/KEY: Primer
<222> LOCATION: (1)..(23)

<400> SEQUENCE: 16
gcagccctaa aatcgcataa agc                                            23

<210> SEQ ID NO 17
<211> LENGTH: 23
<212> TYPE: PRT
<213> ORGANISM: Bacillus lentus
<220> FEATURE:
<221> NAME/KEY: SIGNAL
<222> LOCATION: (1)..(23)

<400> SEQUENCE: 17

Met Lys Lys Pro Leu Gly Lys Ile Val Ala Ser Thr Ala Leu Leu Ile
1               5                   10                  15

Ser Val Ala Phe Ser Ser Ser
            20
```